United States Patent [19]

Klehm

[11] Plant 4,249

[45] May 2, 1978

[54] PEONY PLANT NAMED BRIDAL ICING

[75] Inventor: Roy G. Klehm, Barrington, Ill.

[73] Assignee: Klehm Boys Partnership, Arlington Heights, Ill.

[21] Appl. No.: 795,312

[22] Filed: May 9, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of peony plant distinguished by an almost perfect "bomb" type of white flower which is produced profusely late in the peony blooming season and which has an above average lasting quality, both on the plant and as a cut flower. The plant is of medium height with a rapid growth habit, above average strength, and abundant deep green foliage.

2 Drawing Figures

BACKGROUND OF THE NEW PLANT

My new variety of peony plant was discovered by me in 1967 among a group of seedlings of Charlies White (U.S. Plant Pat. No. 3,684) × Bowl of Cream (U.S. Plant Pat. No. 2,451) grown at Arlington Heights, Ill., in the course of breeding efforts carried on with the object of producing improved peony varieties for the commercial market, particularly strong plants having better blossom color and petalage and a pleasing fragrance. This plant was observed to have a much improved flower form over either of its parents and for that reason was selected by me for propagation and test.

Asexual propagation of this plant, under my direction, at Arlington Heights, Ill., by root division and through several generations has shown this plant to have commercial advantages in addition to its unique flower and that its distinctive characteristics hold true from generation to generation and appear to be firmly fixed.

Commercial scale propagation of this new peony variety by root division is now being done at Champaign, Ill., and at Arlington Heights, Ill.

DESCRIPTION OF THE DRAWING

My new peony plant variety is illustrated by the accompanying photographic drawing which, in full color, shows the new plant and its flower in full bloom. The upper view shows a number of the plants as grown in the field and the lower view is a face view of a fully opened flower showing its form and coloring, the colors shown being as nearly true as it is reasonably possible to obtain by conventional photographic procedures.

DESCRIPTION OF THE PLANT

The following is a detailed description of my new peony plant with color specifications according to the R.H.S. Colour Chart published by The Royal Horticultural Society of London, England, with the collaboration of The British Colour Council, the observations having been made at Arlington Heights, Ill., during the 1976 flowering season.

THE PLANT

Origin: Seedling.

Parentage:

*Seed parent.*—Charlies White (U.S. Plant Pat. No. 3,684).

*Pollen parent.*—Bowl of Cream (U.S. Plant Pat. No. 2,451).

Classification: *Paeonia lactiflora.*

Form: Multi-stem herbaceous bush.

Height: Average —28 to 29 inches.

Growth rate: Rapid.

Growth habit: Upright and sturdy with above average strength.

*Cane size.*—½ to 9/16 inch at base.

Foliage: Quantity — abundant.

*Leaf size.*—Large. Shape: Elliptically acute with smooth margins. Aspect: Smooth and glossy. Ribs and veins: Pronounced. Petioles: 3 to 4 inches long.

*Leaflets.*—Size — 5 to 6 inches long. Number: 5 for each leaf.

*Color.*—Upper side — Forest Green, RHS 135A. Under side — Almond Green, RHS 135B.

THE BUD

Size: Medium large.

Shape: Almost spherical.

*Diameter.*—1¼ inch.

*Depth.*—1¼ inch.

Opening rate: Normal, but completely dependent on weather.

Color:

*When sepals first divide.*—Pure White.

*When petals begin to unfurl.*—Cream White, RHS 158D.

Sepals: Hooded over bud until dividing.

*Aspect.*—Very smooth.

*Color.*—Inside — Limpid Green, RHS 135D. Outside — Medium Green, RHS 135C.

Calyx: Size — Large.

*Shape.*—Polysepalous.

*Aspect.*—Smooth.

*Splitting.*—None.

THE FLOWER

Blooming habit: Profuse and once each year, in mid-season for peony types.

Borne: Singly, with a few axillary buds on each stem.

Size: Medium.

*Diameter.*—About 7½ inches.

*Depth.*—About 3¼ to 3½ inches.

Shape: Cup shaped when bloom first opens becoming a perfect "bomb" shape as guard petals spread.

Petalage: Number of petals — Numerous.

*Arrangement.*—Imbricated.

*Form.*—Spatulate, with round spoon-like and slightly notched guard petals.

*Texture.*—Soft.

*Appearance.*—Satiny.

*Color.*—Outer-guard petals — White body with Cream White base, RHS 155D. Inside petals — Body — White, RHS 158D, with Chrome Yellow base, RHS 15D. Reverse sides — Same as upper sides.

*Persistence.*—Petals persist until end of term and then drop clean from stem.

Petaloids: None.

Discoloration: Depending on weather, bloom fades to pure white after maturity.

Disease resistance: This plant has an average resistance to botrytis and root rot, as observed at Arlington Heights, Ill., and at Champaign, Ill.

Fragrance: Pleasingly mild typical peony.

Lasting quality:

*On plant.*—Above average, 10–15 days.

*As cut flower.*—About 7 to 10 days depending upon treatment and care.

REPRODUCTIVE ORGANS

Stamens: None.

Pistils: 3 in number.

*Styles.*—½ to ¾ inch long.

*Stigmas.*—Color — Cream White.

Ovaries: Generally round in shape.

*Color.*—Beech Brown, RHS 165A, at fertilized maturity.

FRUIT

Fertility: The fruit of this plant is fertile.

Shape: Round.

Color: At maturity — Beech Brown, RHS 165A.

This new variety of peony plant is believed to have the most perfect "bomb" form of flower of any commercial peony. This distinct flower form is further distinguished by the pleasing blend of pure white guards and a creamy white mass of "bomb" petals which is warmed by an inner glow produced by the chrome yellow color of each petal at its base. This new plant possesses luxurious deep green foliage and strong stiff stems so desirable for modern gardens and its blossoms, as cut flowers, readily imbibe water and store well under refrigerated commercial flower storage conditions and procedures.

This new variety enjoys most of the advantageous and distinctive characteristics of its seed parent, Charlies White (U.S. Plant Pat. No. 3,684), the primary distinction over its parent residing in the much improved flower form. Also, this new plant grows to only about two-thirds the height of its seed parent, its flowering time of "mid-season" is much later than that of its seed parent, and the keeping quality of its flowers, while better than average for peonies, is somewhat less advantageous than that its parent enjoys.

I claim:

1. The new and distinct peony plant cultivar substantially as herein shown and described, characterized by its improved and nearly perfect "bomb" type of flowers, and by its profuse production of very white flowers the appearance of which is enhanced by the warm inner glow from the yellow base coloring of the "bomb" petals.

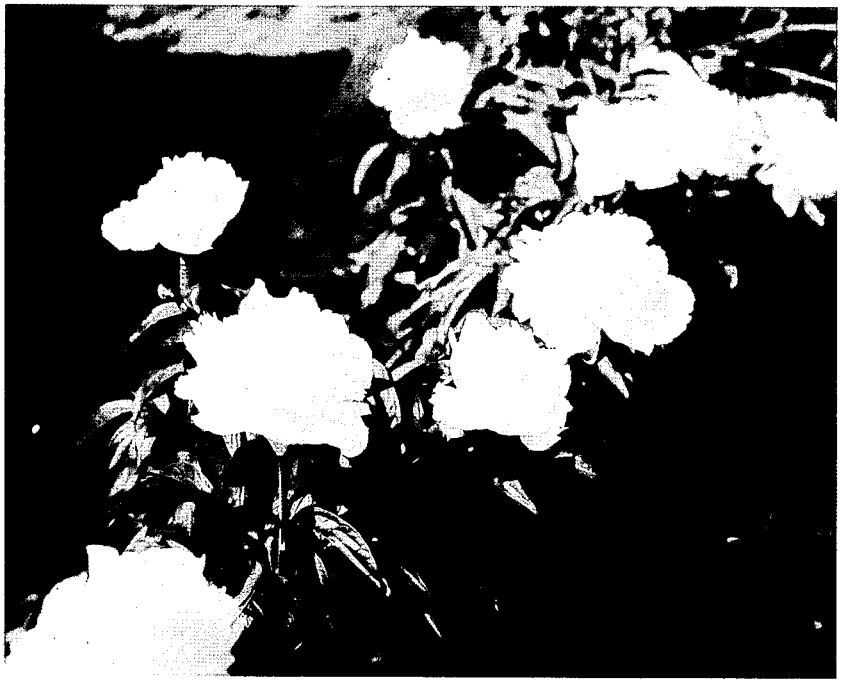
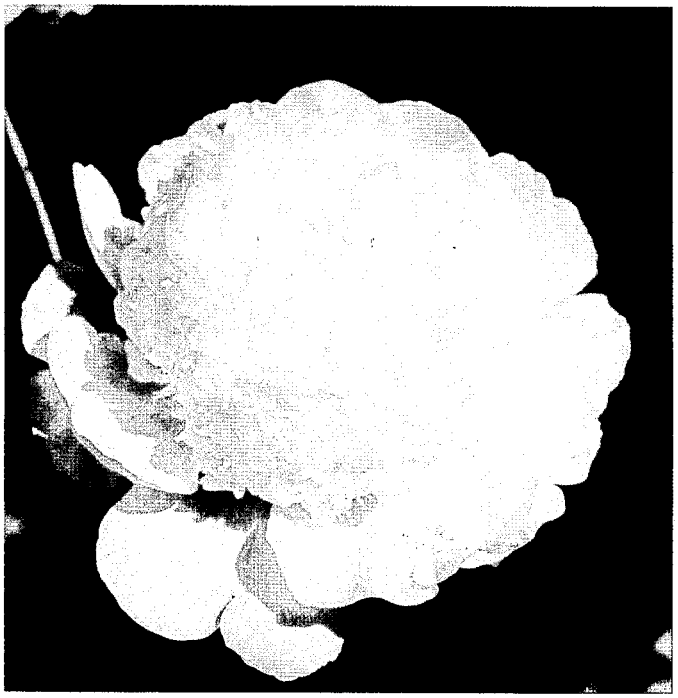

* * * * *